United States Patent
Chang

(10) Patent No.: US 9,295,817 B2
(45) Date of Patent: *Mar. 29, 2016

(54) ENDOLUMINAL DELIVERY OF ANESTHESIA

(71) Applicant: David W. Chang, Sunnyvale, CA (US)

(72) Inventor: David W. Chang, Sunnyvale, CA (US)

(73) Assignee: Silk Road Medical, Inc., Sunnyvale, CA (US)

( * ) Notice: Subject to any disclaimer, the term of this patent is extended or adjusted under 35 U.S.C. 154(b) by 314 days.

This patent is subject to a terminal disclaimer.

(21) Appl. No.: 13/674,792

(22) Filed: Nov. 12, 2012

(65) Prior Publication Data

US 2013/0172852 A1 Jul. 4, 2013

Related U.S. Application Data

(63) Continuation of application No. 13/017,905, filed on Jan. 31, 2011, now Pat. No. 8,308,709, which is a continuation of application No. 11/282,222, filed on Nov. 18, 2005, now Pat. No. 7,879,011.

(60) Provisional application No. 60/629,420, filed on Nov. 18, 2004, provisional application No. 60/664,142, filed on Mar. 21, 2005.

(51) Int. Cl.
*A61M 31/00* (2006.01)
*A61M 25/10* (2013.01)
(Continued)

(52) U.S. Cl.
CPC ............ *A61M 25/10* (2013.01); *A61M 25/0084* (2013.01); *A61M 25/04* (2013.01); *A61M 25/1011* (2013.01); *A61M 2025/009* (2013.01)

(58) Field of Classification Search
CPC ............ A61M 25/0084; A61M 25/04; A61M 25/1011; A61M 25/10; A61M 2025/009
USPC ......................................... 604/500, 508–512
See application file for complete search history.

(56) References Cited

U.S. PATENT DOCUMENTS 5,354,279 A 10/1994 Hofling
5,364,356 A 11/1994 Hofling
(Continued)

FOREIGN PATENT DOCUMENTS

WO WO-00/67646 A1 11/2000
WO WO-2006/055826 A2 5/2006

OTHER PUBLICATIONS

Henry et al. (1999) "Carotid stenting with cerebral protection: First clinical experience using the PercuSurge GuardWire System" *J. Endovasc. Surg.* 6:321-331.

*Primary Examiner* — Matthew F Desanto
(74) *Attorney, Agent, or Firm* — Fred C. Hernandez; Mintz Levin Cohn Ferris Glovsky and Popeo, P.C.

(57) ABSTRACT

Described herein are methods and devices for selectively applying fluids (particularly anesthetics) to a target tissue from within a blood vessel while minimizing the amount of fluid applied to non-target tissue. The injection catheters described herein may include an elongate body, a directional injector, and one or more holdfasts for securing the catheter before extending the injector. The methods of selectively applying anesthetic to a target structure generally include the steps of inserting an injection catheter into a body vessel, positioning the injection catheter within the body vessel near the target structure, anchoring the injection catheter before extending a directional injector from the injection catheter, and applying anesthetic from the injection catheter to the target structure.

8 Claims, 10 Drawing Sheets

(51) Int. Cl.
  *A61M 25/00* (2006.01)
  *A61M 25/04* (2006.01)

(56) References Cited

U.S. PATENT DOCUMENTS

| | | | |
|---|---|---|---|
| 5,419,777 A | 5/1995 | Hofling | |
| 5,464,395 A | 11/1995 | Faxon et al. | |
| 5,478,328 A | 12/1995 | Silverman et al. | |
| 5,681,281 A | 10/1997 | Vigil et al. | |
| 5,693,029 A | 12/1997 | Leonhardt | |
| 5,713,863 A | 2/1998 | Vigil et al. | |
| 5,746,716 A | 5/1998 | Vigil et al. | |
| 5,916,194 A * | 6/1999 | Jacobsen et al. | 604/96.01 |
| 6,102,904 A | 8/2000 | Vigil et al. | |
| 6,210,392 B1 | 4/2001 | Vigil et al. | |
| 6,217,554 B1 | 4/2001 | Green | |
| 6,258,084 B1 | 7/2001 | Goldman et al. | |
| 6,283,947 B1 | 9/2001 | Mirzaee | |
| 6,283,951 B1 | 9/2001 | Flaherty et al. | |
| 6,302,870 B1 | 10/2001 | Jacobsen et al. | |
| 6,312,402 B1 | 11/2001 | Hansmann | |
| 6,319,230 B1 | 11/2001 | Palasis et al. | |
| 6,419,653 B2 | 7/2002 | Edwards et al. | |
| 6,423,032 B2 | 7/2002 | Parodi | |
| 6,458,095 B1 | 10/2002 | Wirt et al. | |
| 6,458,098 B1 | 10/2002 | Kanesaka | |
| 6,595,953 B1 | 7/2003 | Coppi et al. | |
| 6,599,267 B1 | 7/2003 | Ray et al. | |
| 6,685,648 B2 | 2/2004 | Flaherty et al. | |
| 6,692,466 B1 | 2/2004 | Chow et al. | |
| 6,702,744 B2 | 3/2004 | Mandrusov et al. | |
| 6,723,082 B1 * | 4/2004 | Payne et al. | 604/528 |
| 6,752,803 B2 | 6/2004 | Goldman et al. | |
| 6,837,881 B1 | 1/2005 | Barbut | |
| 6,860,867 B2 | 3/2005 | Seward et al. | |
| 6,913,763 B2 | 7/2005 | Lerner | |
| 7,008,411 B1 | 3/2006 | Mandrusov et al. | |
| 7,083,594 B2 | 8/2006 | Coppi | |
| 7,776,025 B2 | 8/2010 | Bobo, Jr. | |
| 7,998,104 B2 | 8/2011 | Chang | |
| 8,308,709 B2 * | 11/2012 | Chang | 604/509 |
| 2002/0072706 A1 | 6/2002 | Hiblar et al. | |
| 2002/0103459 A1 | 8/2002 | Sparks et al. | |
| 2002/0111601 A1 * | 8/2002 | Thompson | 604/514 |
| 2002/0151866 A1 | 10/2002 | Lundkvist et al. | |
| 2002/0183735 A1 | 12/2002 | Edwards et al. | |
| 2003/0032936 A1 | 2/2003 | Lederman | |
| 2003/0135206 A1 | 7/2003 | Edwards et al. | |
| 2003/0233065 A1 | 12/2003 | Steward et al. | |
| 2004/0024371 A1 | 2/2004 | Plicchi et al. | |
| 2004/0044329 A1 | 3/2004 | Trudell | |
| 2004/0122360 A1 | 6/2004 | Waldhauser et al. | |
| 2004/0133154 A1 | 7/2004 | Flaherty et al. | |
| 2004/0138562 A1 | 7/2004 | Makower et al. | |
| 2004/0186435 A1 | 9/2004 | Seward | |
| 2004/0204675 A1 | 10/2004 | Seward et al. | |
| 2004/0215181 A1 | 10/2004 | Christopherson et al. | |
| 2005/0154344 A1 | 7/2005 | Chang | |
| 2005/0154349 A1 | 7/2005 | Renz et al. | |
| 2005/0182385 A1 | 8/2005 | Epley | |
| 2006/0106338 A1 | 5/2006 | Chang | |
| 2006/0129125 A1 | 6/2006 | Copa et al. | |
| 2011/0125131 A1 | 5/2011 | Chang | |

* cited by examiner

ENDOLUMINAL DELIVERY OF ANESTHESIA

RELATED APPLICATIONS

This application is a continuation of co-pending U.S. patent application Ser. No. 13/017,905, entitled "Endoluminal Delivery Of Anesthesia," filed, Jan. 31, 2011, which in turn is a continuation of U.S. patent application Ser. No. 11/282,222, entitled "Endoluminal Delivery Of Anesthesia," filed Nov. 18, 2005, now U.S. Pat. No. 7,879,011, which claims the benefit under 35 U.S.C. §119(e) of the following U.S. Provisional Applications: (1) U.S. Provisional Patent Application Ser. No. 60/629,420, filed Nov. 18, 2004; and (2) U.S. Provisional Patent Application Ser. No. 60/664,142, filed Mar. 21, 2005. Priority of the aforementioned filing dates is hereby claimed, and the disclosures of the Applications are hereby incorporated by reference in their entirety.

This application is also related to U.S. patent application Ser. No. 10/996,301, filed Nov. 22, 2004, entitled, "Method and Apparatus for Treating a Carotid Artery" by David W. Chang, which is also incorporated herein by reference in its entirety.

FIELD

The devices, systems and methods described here are in the field of percutaneous surgery, and particularly the area of anesthetic delivery to specific tissue regions to assist with angioplasty or tissue ablation.

BACKGROUND

Minimally invasive surgeries (e.g., percutaneous surgeries) account for an increasing number of medical procedures. These surgeries may result in less patient trauma and may yield a significant cost savings as a result of shorter hospitalization times and reduced therapy requirements. Percutaneous procedures include endoscopic and catheter-based procedures such as angioplasty (e.g., balloon angioplasty), stent delivery, and tissue ablation. In many of these procedures, pain, and even tissue damage, can be reduced or eliminated by targeting delivery of anesthesia to the nerves or other tissues adjacent to the vessel in which the procedure is taking place.

Examples of two treatments that could benefit from the controlled application of anesthetic to specific tissues include angioplasty and tissue ablation. For example, carotid angioplasty and stenting can result in stimulation of the carotid sinus nerve, which can lead to bradycardia and hypotension, since acutely stretching or manipulating the carotid artery (which commonly occurs during angioplasty of this region) impinges on the sinus nerve. This can cause profound bradycardia or asystole, leading to severe drop in blood pressure. Patients with severe coronary artery disease or aortic stenosis may suffer cardiac arrest with hypotension. Stent placement can also cause prolonged distention of the carotid artery resulting in continuous stimulation of the carotid sinus nerve, and may require treatment with vasopressor medications requiring observation in an intensive care setting.

Similarly, the treatment of tissue within a vessel by ablation (e.g., using an ablation catheter), may deleteriously effect nearby tissue structures. Ablation of tissue from within the vessel lumen heats even non-target, e.g., adjacent tissue due thermal diffusion from the application of energy (e.g., electrical energy). This heat may cause pain or trauma. The use anesthesia, particularly tumescent anesthesia, is one method of reducing the negative effects of endoluminal ablation.

Tumescent anesthesia typically involves providing local anesthesia to a surgical site using dilute local anesthetic solution to both numb and "inflate" the tissue around the target ablation zone. Historically, the delivery of anesthetic in tumescent anesthesia is accomplished by percutaneous introduction of the anesthetic with a hypodermic needle (e.g., see U.S. Pat. No. 6,258,084 to Goldman, et al., herein incorporated by reference in its entirety). This method is time consuming and requires repeated puncture of the skin if a significant surface area must be treated. Moreover, direct targeting of the structures to be rendered anesthetic may be diffuse and inaccurate, resulting in higher volumes and dose of anesthetic. Ideally, the tumescent anesthesia method would apply fluid (including fluid with anesthesia) to the perivesicular (or periluminal) region immediately surrounding the vessel in which the ablation catheter is positioned. In particular, the region around the blood vessel (e.g., between the endothelium and the subendothelial connective tissue) may be selectively injected with a solution of anesthetic to optimize the effectiveness of tumescent anesthesia.

Although many medical procedures (including angioplasty and tissue ablation as described) may benefit from the precisely controlled application of anesthetics, most practitioners continue to apply anesthesia with only limited specificity. Even when performing catheter-based minimally invasive surgery, may practitioners apply anesthesia either systemically (e.g., applying it to the entire patient) or by injecting the anesthesia into the appropriate body region using a needle. However, such percutaneous puncture results in difficult and imprecise deliver of anesthetic. This may also lead to injury of adjacent structures including the veins, arteries, nerves, musculature, etc. Furthermore, imprecise injection can also result in dislodging plaque, leading to thrombosis or other complications. These problems may be avoided by the precise delivery of anesthetic from within the lumen of a vessel.

Unfortunately, most devices for releasing drugs from within the lumen of a body vessel that are currently known, including most injection catheters and infusion catheters, suffer from various inadequacies that make them less than optimal for the precise delivery of anesthesia to different body regions. For example U.S. Pat. No. 6,210,392 to Vigil et al. describes an injection catheter for injecting fluid into a treatment area of a vessel wall. Similarly, U.S. Pat. No. 6,685,648 to Flaherty et al. describes a system and method for delivering drugs using a catheter having a deployable puncturing element. Other examples of injection catheters can be found in U.S. Pat. No. 6,458,098, U.S. Pat. No. 6,692,466, U.S. Pat. No. 5,354,279, U.S. Pat. No. 6,302,870, and U.S. Pat. No. 5,693,029. Each of the above-mentioned patents is herein incorporated by reference in its entirety.

Many of the injection catheters described in these patents do not allow precise control of the stability of the catheter and/or the injector, and therefore may have problems controlling the amount and location of material (particularly anesthetic) applied. Stability of the injection catheter is particularly important when it is desirable to apply a fluid (e.g., a fluid containing an anesthetic) to a precise location outside of the vessel lumen. Movement of the catheter caused by deploying the injection port may prevent proper delivery of the fluid, and may lead to damage of the vessel or extravesicular structures. This may be particularly true when the wall of the vessel is difficult to penetrate (e.g., because of plaque such as arterial plaques, etc.), or is irregularly shaped. Precise delivery of fluid allows for the selective use of normal tissue planes (e. as channels for distribution of the fluid, further enhancing the specificity and decreasing damage to the tissue.

Thus, there is a need for methods and devices for delivering fluids and/or anesthetics to precise locations adjacent to a body vessel from within the vessel. The devices, methods and systems described herein address this need, and the problems described above.

SUMMARY

Described herein are methods and devices for selectively and precisely applying fluid (particularly fluid containing anesthetics) to a target tissue from within a body vessel without substantially applying anesthetic to non-target structures. These methods and devices may be used to deliver anesthetic at precise locations even within active vessels (e.g., blood vessels) and even when the dimensions of the vessel are unknown, or the wall of the vessel is occluded or congested.

In one variation of the method of selectively applying anesthetic to a target structure, the method selectively applies anesthetic from within a body vessel without substantially applying anesthetic to non-target structures. In general, the method includes the steps of inserting an injection catheter into a body vessel (wherein the injection catheter comprises a directional injector configured to apply anesthetic selectively to the target structure), positioning the injection catheter within the body vessel near the target structure, anchoring the injection catheter before extending the directional injector to selectively deliver anesthetic to the target structure, and selectively applying anesthetic from the injection catheter to the target structure. Any appropriate injection catheter may be used as part of this method, particularly injection catheters capable of directional application of fluid as described herein.

The method of selectively applying anesthetic to a target structure may also include visualizing the injection catheter. For example, the injection catheter may be visualized by fluoroscopic visualization, ultrasound, or any other technique or combination of techniques. The injection catheter or portions of the injection catheter (e.g., the extendable directional injector) may be marked so that it can be readily visualized. In some variations, the application of anesthetic to the target structure can be visualized (e.g., by including a maker or contrast agent that is readily visualized by an appropriate visualization method). For example, the marker or contrast agent (such as a radiopaque material) may be added to the anesthetic when it is released to monitor how effectively the anesthetic is applied to the target structure.

The injection catheter may be inserted through any appropriate opening into a body vessel. The injection catheter may be used as part of any percutaneous procedure. For example, the injection catheter may be inserted from an incision in the femoral vein of the groin or through a transcervical incision. Although the body vessels described herein are mostly blood vessels (e.g., veins and arteries), the methods and device described herein may be applied to any appropriate body vessel, including non-blood vessels (e.g., urinary tracts, lymphatic vessels, etc.).

The injection catheter may be positioned within the body vessel near the target structure so that the injection catheter can access the target structure from within the lumen of the vessel by extending the injector. Positioning may include orienting the catheter. For example, the injection catheter may be advanced within the vessel, withdrawn down the vessel, rotated within the vessel, or moved laterally within the vessel. In some variations, the injection catheter used is adapted to allow the entire catheter, or a region of the catheter, to be manipulated to position the injector so that it can reach the target structure. Visualization of the catheter and/or the region surrounding the catheter (including the target structure) may be used to help position the injection catheter, as described above.

Typically, the injection catheter is positioned before it is anchored. However, in some variations, the injection catheter may be only approximately anchored, and then the position of the injector portion of the catheter may be adjusted to precisely orient the injector. In these variations, the injector portion includes a region that is adjustable to change the location or orientation of the injector even when the rest of the injection catheter is secured in place. For example, the injector may be rotated or moved (e.g., forward/backwards) with respect to the anchored injection catheter. The injector may also be independently extendable from the injection catheter, as described below. In some variations, the injector and/or regions of the injection catheter that allow modification of the orientation of the injector can be modified, secured or locked into position.

In general, the injection catheter is anchored before extending the directional injector to selectively deliver anesthetic to the target structure. Anchoring the injection catheter may prevent unwanted movement of the injection catheter and therefore the injector. Movement of the injection catheter and resultant movement of the injector may change the position of the injector with respect to the target structure, or it may even damage the target structure. The methods and devices described herein allow precise positioning of the injector and therefore injection of anesthetic in very exacting locations such as between tissue fascia, or around the sheath of a nerve without impinging on the nerve. Anchoring may stabilize the injection catheter. Anchoring may be particularly useful because force may be required to extend the injector. For example, force may be required to penetrate the wall of the vessel (particularly if there are deposits such as plaque on the vessel) or adjacent structures. The anchored injection catheter may therefore allow leverage for extending the injection catheter.

In some variations, the step of anchoring the injection catheter involves using one or more holdfasts to secure the injection catheter (particularly the region of the injection catheter from which the directional injector extends) within the vessel. A holdfast may be any feature that is configured to anchor at least a portion of the injection catheter to prevent it from moving or shifting orientation with respect to the vessel and any extraluminal structures adjacent to the vessel. For example, a holdfast may include a stiff member, a brace, an inflatable balloon, a suction port, an expandable scaffold, a magnetic lock, etc. The holdfast may be deployed by a practitioner once the injection catheter is in a desired position. For example, in one variation, the injection catheter is anchored by inflating a balloon connected to the injection catheter to secure the injection catheter within the body vessel. In another variation, the injection catheter is anchored by deploying a stiff member that couples with the injection catheter. For example, a stiff or stiffenable rod may be inserted into a lumen of the injection catheter once it is in position. Thus, the stiff member can secure the injection catheter in place, and provide a stable support or brace for the injector. Alternatively, the injection catheter may be configured of (or include) a stiff material. Multiple anchors may be used with a single injection catheter.

The injector may be extended from the body of the injection catheter by a practitioner. In some variations, the injector is contained within the body of the injection catheter, and exits from a port on the side or the end of the injection catheter. This port may be closed until immediately before extending the injector, or it may be an opening that is always open. Extension of the injector may be controlled (e.g., guided) by structures in the injection catheter. For example, the injector may be keyed to the shape of the port on the injection catheter to prevent undesirable movement of the injector with respect to the injection catheter. For example, a portion of the injector may have a cross-sectional shape (e.g., triangular) that mates with a channel in the injection catheter to prevent rotation. The injector may be manually extended or automatically extended. The injector and injection catheter may also be structured to limit the distance and/or rate that the injector extends. The step of extending the directional injector may include monitoring the orientation of the directional injector so that the directional injector can be extended to apply fluid to the target structure.

Anesthetic may be applied from the injector in any appropriate fashion. The injector may be a directional injector, which may apply fluid (including fluid with anesthesia) in an appropriate direction. Examples of directional injectors are described herein, but may include injectors configured to apply fluid in directions that are off-axis from the direction of extension of the injector into the target tissue, and injectors configured to apply fluid in a planar fashion or with a minimum or maximum pressure. Also described are directional injectors that apply fluid in a direction that is opposite to the direction of extension of the injector (e.g., in the proximal direction of the injector). Generally, the step of applying fluids such as anesthetics (or solutions including anesthetics) may include applying pressure distally to release anesthetic from the injector. The step of applying may mean specific application of the fluid into the target tissue or region while substantially avoiding the application of fluid to non-target regions. Any appropriate fluid can be used, including fluids with anesthetics. Examples of anesthetics that may be used include Benzocaine, Mepivacaine, Ropivacaine, Bupivacaine, Lidocaine, Prilocaine, Procaine, Chloroprocaine, etc.

The methods described herein may be used with any appropriate target structure or tissue region. For example, the target structure may comprise a nerve, or a sheath around a nerve, to provide local anesthesia. In one variation, the target structure is the sinus nerve adjacent to the carotid artery.

One variation of the methods described herein is a method of selectively applying anesthetic to a subject's sinus nerve from within the carotid artery. The method includes the steps of inserting an injection catheter into the carotid artery (wherein the injection catheter comprises a directional injector configured to apply anesthetic selectively to the sinus nerve), positioning the injection catheter within the carotid artery near the sinus nerve, anchoring the injection catheter before extending the directional injector to selectively deliver anesthetic to the sinus nerve, and applying anesthetic from the injection catheter to the sinus nerve.

Providing anesthetic to nerves is particularly useful during intravascular procedures near the nerve. For example, during angioplasty procedures, it may be useful to provide anesthetic to nearby nerves (such as the sinus nerve) before beginning the angioplasty procedure or selectively after the angioplasty procedure.

Also described herein is a method of selectively applying anesthetic to a target tissue from within a blood vessel while minimizing the amount of anesthetic applied to non-target tissue. This method includes the steps of inserting an injection catheter into a blood vessel, positioning the injection catheter within the blood vessel adjacent to the target tissue by visualizing the directional injector and the target tissue, and applying anesthetic from the injection catheter to the target structure. The injection may have a directional injector configured to controllably release anesthetic, and a holdfast for anchoring the injection catheter within the blood vessel. Other variations of the injection catheter are also described herein.

An injection catheter may be used to selectively inject material to a target structure adjacent to a body vessel. The injection catheter may comprise an elongate body having a distal and a proximal end, a holdfast near the distal end for anchoring the injection catheter within a body vessel, and an extendable directional injector having a distal end and a proximal end, the directional injector extendable from the elongate body, wherein the directional injector comprises a tissue-penetrating section at the distal end and a fluid delivery section located proximal to the tissue-penetrating section. The fluid delivery section may be configured to deliver fluid in a direction that is different from the direction of tissue penetration (including the direction opposite from the direction that the injector extends).

The injection catheter may also include markers for visualizing the extension of the extendable directional injector 621 (referring to FIG. 6). The injection catheter may also be configured to limit or control the amount (or rate) that the injector is extended. In some variations, the injection catheter includes a fine adjustment region which allows the injector to be oriented even after anchoring the injection catheter within the vessel.

As mentioned, one or more holdfasts may be used with the injection catheter, or may be integral to (e.g., part of) the injection catheter. For example, the injection catheter may include one or more inflatable balloons. The holdfast may be positioned distally and/or proximally to the port from which the injector exits the injection catheter, or they may be at the same axial position as the port along the injection catheter length. In some variations, the holdfast comprises a rigid or stiff member (or a member than may be rigidifiable), a brace, an inflatable balloon, a suction port, an expandable scaffold, a magnetic lock, etc. The holdfast is deployable so that the injection catheter is allowed to move within the vessel when the holdfast is not engaged, but once the holdfast is engaged it substantially prevents movement of the injection catheter within the vessel.

Any appropriate injector may be used. Most injectors include one or more penetrating sections for penetrating the wall of the vessel and any other structures between the injection catheter and the target tissue. The penetrating section of the injector may be sharp or substantially dull. In some variations, the penetration section comprises a beveled edge. An injector may also include one or more openings for passing fluid out of the injector into the tissue from a fluid delivery section. For example, the injector may have a fluid delivery section comprising an opening that is in fluid connection with a lumen passing through at least a portion of the directional injector. The fluid delivery section may be configured so that the fluid is released in a desired manner (e.g., from a desired direction, or in a pattern such as a sheet or spray).

Also described herein are methods of selectively applying fluid from within a blood vessel into the perivesicular space to create tumescence. These methods may include inserting an injection catheter into a blood vessel (wherein the injection catheter has an extendable directional injector configured to controllably release fluid), positioning the injection catheter within the blood vessel by visualizing the directional injector, extending the directional injector to pierce the vessel wall, and controllably applying fluid from the injection catheter to the perivesicular space. The fluid injected to create tumescence may include an anesthetic (e.g., "tumescent anesthesia").

DETAILED DESCRIPTION

Figure 1A:
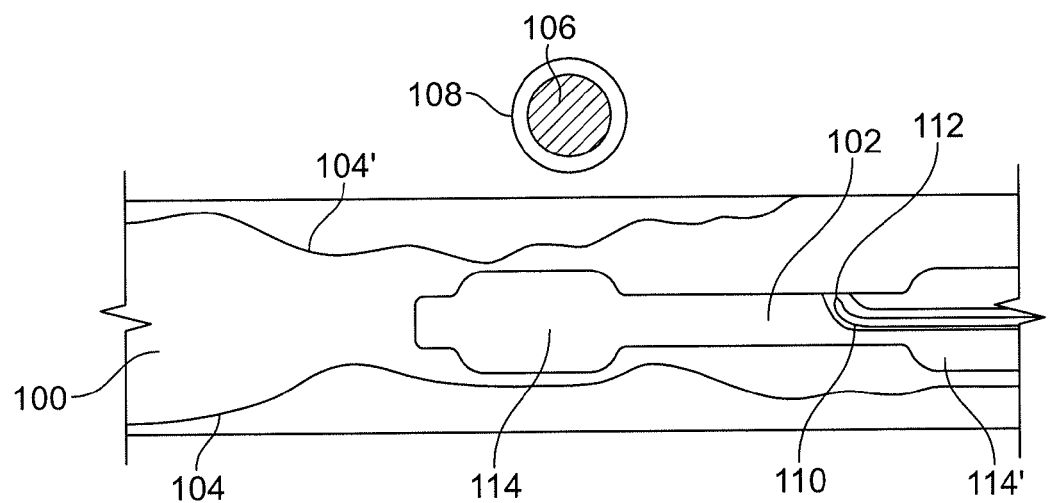
FIGS. 1A-1D illustrate one variation of the methods and devices described herein.

Described herein are methods and devices for selectively applying fluids (particularly anesthetics) to a target tissue from within a blood vessel while minimizing the amount of fluid applied to non-target tissue. The injection catheter devices (or components of these devices) may generally be used to perform the methods for selectively applying fluids to target tissues.

The methods of selectively applying anesthetic to a target structure generally involve positioning the injection catheter (also referred to herein as simply a "catheter") within the body vessel near the target structure, anchoring the injection catheter to stabilize it and to provide support or leverage for an extendable injector, then extending the injector and applying a fluid from the injection catheter to the target structure.

The injection catheters described herein have an elongate body, a directional injector, and a holdfast to secure the injection catheter within the vessel. The combination of these features results in a device that can selectively and precisely apply fluid to a target site outside of the vessel lumen in which the injection catheter is positioned. As described more fully below, these injection catheters can remain stable even when manipulating the injector to penetrate tissue between the injection catheter and the target tissue. Furthermore, these injection catheters may control the way that fluid is applied near or on the target tissue to prevent damage to the target tissue or more proximal tissues.

Although many of the examples provided herein refer to the application of anesthetics or fluids containing anesthetics, any appropriate fluid may be used, with or without anesthetics. For example, fluids may be include saline, or solutions containing drug or therapeutics (e.g., proteins, enzymes, small molecules, antibody-based therapeutics, nucleotide-based therapeutics, etc.). When anesthetics are used, any appropriate anesthetic may be used, including Benzocaine, Mepivacaine, Ropivacaine, Bupivacaine, Lidocaine, Prilocaine, Procaine, Chloroprocaine, etc.

Methods

As described above, the method of selectively applying fluid to a target structure selectively delivers fluid from an injection catheter within a body vessel to the target tissue without substantially applying fluid to non-target structures. This can be accomplished in four steps: (1) inserting an injection catheter into a body vessel, (2) positioning the injection catheter within the body vessel near the target structure, (3) anchoring the injection catheter before extending the directional injector to selectively deliver fluid to the target structure, and (4) applying fluid from the injection catheter to the target structure. Any appropriate injection catheters may be used, particularly the injection catheter described herein.

The injection catheter may be inserted into any appropriate opening into a body vessel or lumen. For example, the injection catheter may be inserted as part of any percutaneous procedure (e.g., through the subject's skin into the vasculature) so that the vessel is a blood vessel (e.g., artery or vein), or into any other appropriate vessel in the body. For example, the injection catheter may be inserted into a lymph vessel, the intestinal tract, etc. Insertion and/or placement of the injection catheter may be manual (e.g., it may be advanced by hand), assisted, or automatically (e.g., robotically). The injection catheter may be used with additional devices to assist in placement and positioning. For example, insertion may involve the use of a sheath or guidewire. Thus, a flexible guidewire may be advanced to a location in the body, and the injection catheter may be advanced along the guidewire through the body until it reaches the correct position.

One example of a surgical method that may benefit from the methods and devices described herein is the TOPS method for treating a carotid artery, as described in the related U.S. patent application Ser. No. 10/996,301, previously incorporated by reference in its entirety. In this example the catheter is inserted through a transcervical incision and positioned within the carotid artery. As described more completely in this application, the catheter may be used to shunt blood from the internal carotid artery to a lower pressure reservoir, allowing treatment of lesions in the carotid artery without distal embolization. The catheter used in this procedure may include an injector for applying anesthesia (e.g., to the nearby sinus nerve), minimizing pain, risk, and potential trauma from the TOPS procedure.

Once the injection catheter (or "catheter") is inserted into the body vessel, it is advanced to a position in the body vessel adjacent or near the target tissue. At any time during the procedure one or more sensing techniques may be used to assist the practitioner (e.g., doctor, nurse, etc.) in positioning and controlling the injection catheter. For example, the catheter may include one or more sensors (e.g., cameras, ultrasound transducers, etc.) on it to detect the position in the subject's body, or to allow for an external device to locate the catheter. The catheter and the subject's body may also (or alternatively) be visualized using any appropriate visualization technique. For example, the subject's body may be visualized using a fluoroscope, an ultrasound, etc. A "subject" may be anyone in need of treatment, including medical patients. Subjects may include humans and animals.

To aid in visualizing the position of the injection catheter within the subject's body, any appropriate contrast agent or marker may be used. The contrast material may be matched to the type of imaging modality used (e.g., radiopaque materials may be used, fluorescent dyes, etc.). In addition, fluid delivered by the injection catheter may also contain a contrast agent or maker, to allow monitoring of the delivery of the fluid within the subject's body. For example, a contrast agent may be used with the anesthetic solution. Thus, the practitioner can confirm that the material has been correctly applied. In some variations, a small amount of fluid (even without anesthesia) may be applied to confirm that the injection catheter has been correctly positioned.

The injection catheter should be positioned near the target structure so that the injection catheter can access the target structure from within the lumen of the vessel by extending the injector. The step of positioning the injection catheter may include advancing, withdrawing and otherwise orienting the injection catheter. For example, the injection catheter may be advanced within the vessel, withdrawn from the vessel, rotated within the vessel, or moved laterally within the vessel. In some variations, the injection catheter is manipulated by controlling the proximal end of the injection catheter.

Manipulation of the injection catheter initially involves a "rough" positioning to place the catheter near the target site within the subject's body. In some variations, once the catheter has been roughly positioned within the proximity of the target tissue, it can be more accurately positioned by fine positioning after it has been secured into position within the vessel by a holdfast. Positioning the catheter within the vessel may also be done iteratively. For example, the catheter may be positioned, secured into place with the holdfast, and then unsecured and moved to reposition the catheter.

The step of positioning the catheter may mean positioning the injector (or injectors) of the injection catheter so that the injector can access the target tissue. For example, in variations of the injection catheter having an elongate injector that extends from an exit port or recess in the body of the catheter, the catheter may be positioned so that the exit port for the injector is adjacent to the target tissue, allowing the injector to be extended from the injection catheter and into the target tissue. In some variations of the injection catheter, the rough positioning of the injection catheter is adequate for this purpose. In other variations, the injection catheter may include a fine positioning region (or an injector positioning region) that may be controllably manipulated to allow limited positioning of the injector even after the injection catheter has been secured into position by a holdfast.

An injector positioning region may be a region of the injection catheter (e.g., encompassing the exit port) that can controllably slide (proximally and/or distally) over a limited distance on the injection catheter, and may also rotate (e.g., around the circumference of the injection catheter). The movement of this region may be controllable by the user from the proximal end of the catheter. In some variations, the angle that the injector exits the injection catheter may be controlled to "aim" the tip of the injection within a set radius (e.g., within about ±20° from a direction normal to the long axis of the injection catheter). Aiming the injector in this way may be accomplished by changing the position of the exit port with respect to the rest of the injection catheter, and/or changing the angle of a deflection plate (described further below) which changes the trajectory of some types of injectors so that they may exit the injection catheter from a lumen within the injection catheter.

Once the injection catheter is at least roughly positioned, it is anchored or secured into position within the vessel, to prevent substantial movement of the injection catheter with respect to the vessel. As described further in the section discussing injection catheters, any appropriate holdfast (or combination of holdfasts) may be used, including inflatable balloons, suction ports, braces, clamps, adhesives, rigid or rigidifiable members, expandable scaffolds, magnetic locks, etc. In essence, the holdfast should be prevent the catheter from moving due to gross movements (e.g., flow of fluids within or around the catheter, mechanical motion of the subject, etc.), potentially changing the position of the injector with respect to the target tissue. The holdfast may also prevent changes in the relative position of the injector and the target tissue as fluid (e.g., anesthetic) is applied, since the application of fluid to the target tissue can result in localized swelling and distension of the tissue. In variations of the injection catheter having a fine positioning control, an additional "lock" may be provide to secure the fine controls in a fixed position once the injector has been correctly positioned so that it can be extended to contact the target tissue.

The target tissue may be any appropriate tissue or body region as described above. In particular, the target tissue is a tissue that is located adjacent to a vessel which may receive the injection catheter and is within the extension range of the injector (particularly the fluid delivery section of the injector). For example, the target may comprise a nerve, or a sheath around a nerve. In the variation descried in Example 1, below, the target structure is the region surrounding the sinus nerve. In some variations, the target may be a tissue layer or fascia, such as the layers between vessels or other regions of body organs. For example, it may be desirable to inject anesthetic specifically within such a layer before performing a surgical procedure (e.g., ablation) on the tissue or adjacent tissue.

The injection catheter is anchored before extending the injector because the movement of the injection catheter as it is being extended may otherwise disrupt the position of the injection catheter as the injector pushes against the tissue. This is particularly problematic when extending the injection catheter into resilient tissues that resist penetration, or tissues having plaques (e.g., atherosclerotic plaques). Anchoring the injection catheter into position within the vessel can provide leverage so that the injector can apply force to penetrate the tissue and reach the target, without substantially changing the position of the injection catheter. In some variations, the holdfast may itself act as a support or brace for the injector.

The practitioner typically extends the injector from the body of the injection catheter. In some variations, the injector is contained within the body of the injection catheter, and exits from an exit port on the side or the end of the injection catheter. The injector may be manually or automatically extended. The injector and injection catheter may also be structured to limit the distance and/or rate that the injector extends. Once the injector is extended and positioned in, near, or on the target tissue, fluid may be applied. In some variations, the fluid applied is an anesthetic solution. Fluid is typically applied by supplying pressure (e.g., from a syringe, pump, etc.) to the proximal end of the catheter, pushing fluid (which may be preloaded into the injector before positioning) from the injector into the tissue. The amount of pressure used to apply the fluid may be regulated at the proximal end, or the injector itself may include a structure (e.g., a filter, buffer, etc.) to limit the force which fluid exits the injector.

Any of the injectors described herein may be directional injectors, as described further below. In general, a directional injector applies fluid in a selected direction. For example, the directional injector may apply fluid in a direction that is perpendicular to the direction of extension of the injector or opposite the direction of extension of the applicator. In some variations, the directional injector applies fluid from a fluid delivery section that is located on the side of the injector. The injector may be adapted to apply fluid in a plane (e.g. parallel to the injection catheter).

FIG. 1 illustrates one variation of the method for selectively applying anesthetic to a target structure. In FIG. 1A, an injection catheter 102 is located within the lumen of a vessel 100. The walls of the vessel are irregular 104, 104' (e.g., as might be found in an artery or other vessel). Adjacent to a portion of the vessel is a structure 106 surrounded by a sheath 108. The injection catheter includes an injector 110 which can exit the injection catheter from an exit port 112. The injection catheter also includes two holdfasts, here configured as inflatable balloons 114, 114' on either side of the exit port 112 for the injector 110.

Figure 1B:
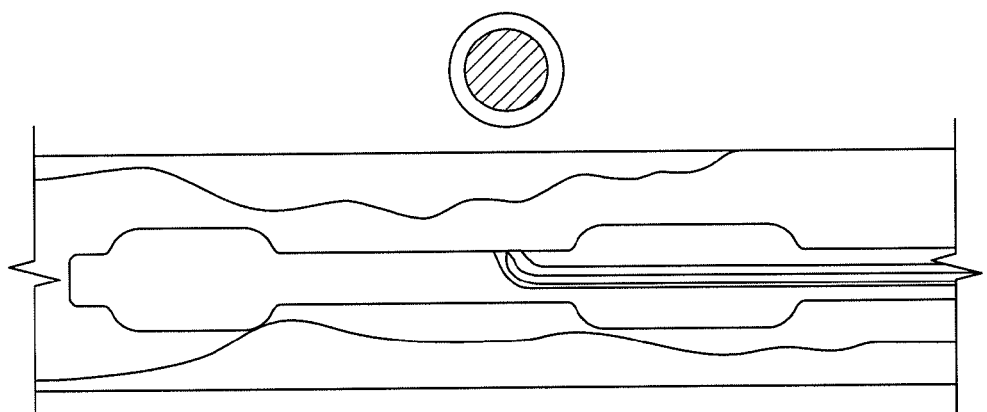
Figure 1C:
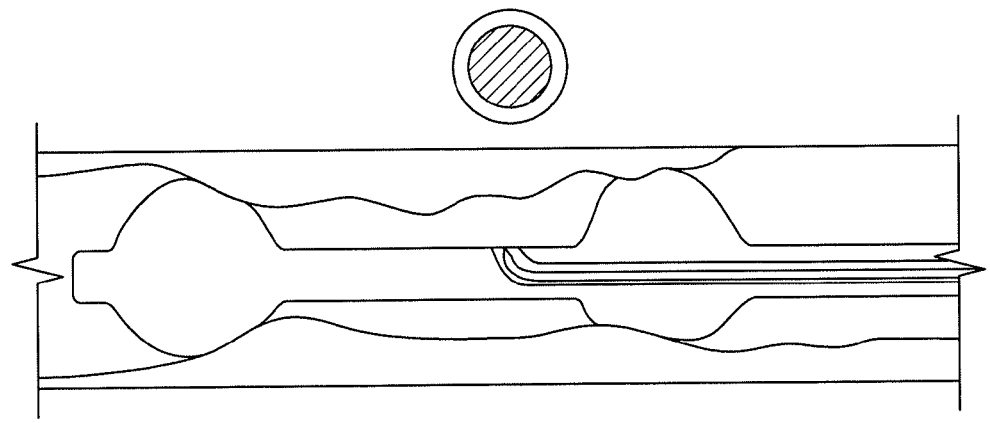

In the transition between FIG. 1A and FIG. 1B, the injection catheter 102 is positioned so that the exit port 112 for the injector 110 is positioned near the target tissue 106, 108. In FIG. 1, the target tissue is area adjacent to the sheath 108, surrounding the structure 106. For example, the structure may be a nerve or nerve bundle (shown in cross-section) surrounded by a nerve sheath. In some variations, the target may be the sheath 108 surrounding the structure 106. Thus, in FIG. 1B, the injection catheter has been positioned with respect to target. The holdfasts (balloons 114, 114') are then deployed, in this example by inflating them to secure the position of the injection catheter within the vessel, as shown in FIG. 1C. The holdfast balloons provide support against the uneven walls of the vessel 104, 104' and prevent the vessel from moving. The balloon-type holdfasts shown in FIG. 1 expand radially around the injection catheter, and therefore may serve to center at least this portion of the injection catheter within the center of the vessel lumen. The balloon (or other holdfast) may also be asymmetrically positioned, so that it preferentially secures the injection catheter to one side of the vessel (e.g., maintaining the shortest distance between the injector and the target tissue). Although two holdfasts are shown in FIG. 1, it should be clear that no holdfast may be used, or that only one holdfast may be used, although in some variations more than one holdfast may be used (as shown). Furthermore, the position of the holdfast with respect to the exit port 112 for the injector 110 may also vary. In some variations, the holdfast may surround the exit port (and may include a passage for the injector). In some, variations the holdfast (or holdfasts) is located proximally or distally to the exit port for the injector.

Figure 1D:
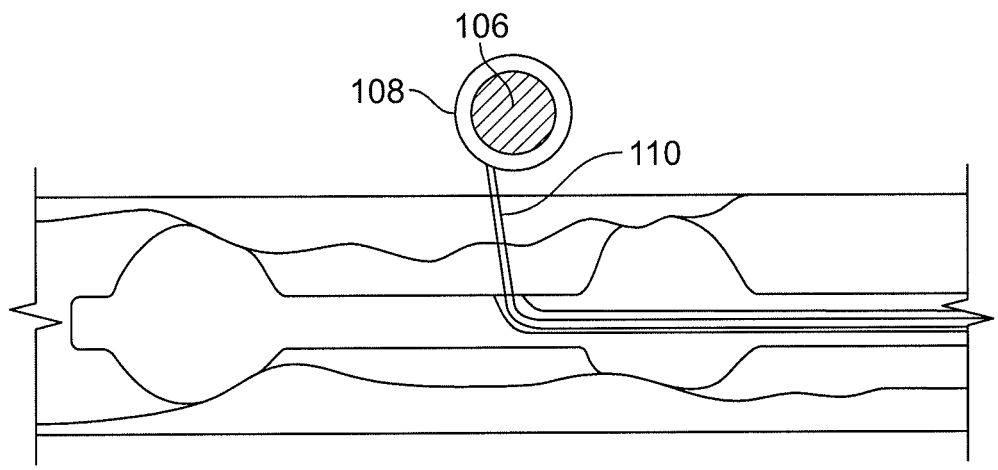
Figure 1E:
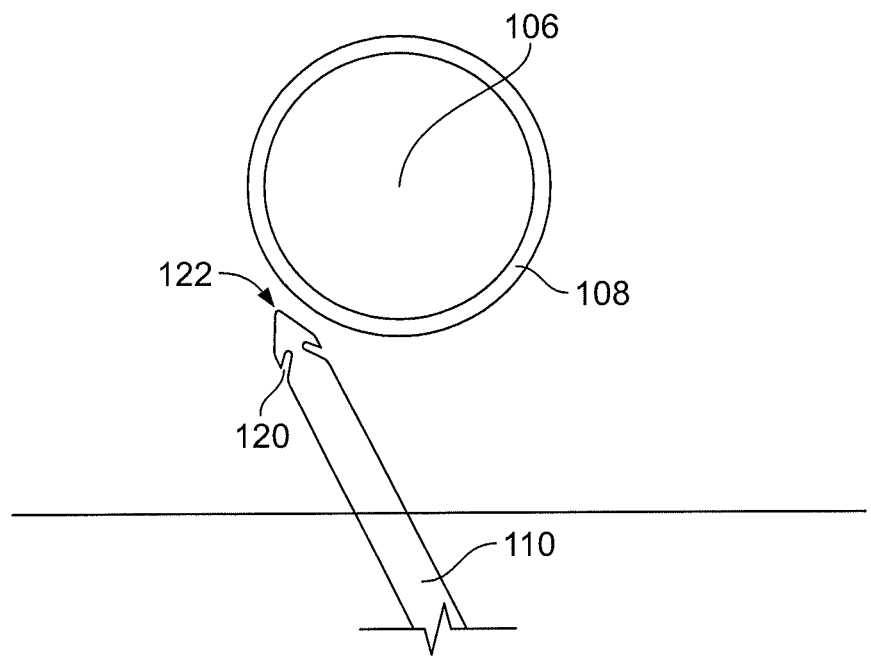
FIG. 1E shows an enlarged view of one portion of FIG. 1D.

Once the injection catheter has been secured into position so that the exit port 112 for the injector 110 is located within reach of the target when the injector 110 is extended, the injector may be extended through the vessel toward the target tissue or structure, as shown in FIG. 1D. The injector is extended from the injection catheter (through the exit port) until it penetrates the vessel and approaches the target 108. The tip of the injector 122 is a tissue-penetrating region. In FIG. 1E, this tip is pointed, and has a relatively small gauge (e.g., greater than a 22 gauge needle) so that it can readily penetrate the tissue. Proximal to the tip along the injector is the fluid delivery section of the injector 120. The fluid delivery section is positioned near or in the target tissue 108, as shown in the enlarged view in FIG. 1E. Once the fluid delivery section of the injector 120 is properly positioned, fluid (e.g., anesthetic) may be injected.

In some variations, the target tissue is a layer or fascia of tissue or a region between structures. The injection catheter and directional injectors described herein may be used to specifically apply fluid between such tissue layers. Because the flow of fluid from the injector may be specifically directed in a direction parallel with the tissue layer (e.g., by matching the fluid delivery section of the injector with the direction of the tissue layer, and/or by using injectors that regulate the rate or force that fluid is applied).

Additional examples of the methods are provided below.

Injection Catheters

In general, the injection catheters described herein include an elongate body, a directional injector that is extendable from the elongate body to penetrate tissue and deliver fluid in a direction that is different from the direction of tissue penetration, and a holdfast for securing the injection catheter within the vessel, providing support and stability to the injector.

The injection catheter typically has an elongate body with a distal and a proximal end. The body generally has one or more lumens along at least a portion of its length (e.g., from the proximal end to at least the exit port for the injector. The body may include at least one passage through which one or more injectors are connected to a pressure or fluid source. In some variations, the body includes additional passages, as for a guidewire, endoscope, steering cable(s), or the like. The body may be made of any appropriate material or materials, and may be flexible, jointed, stiffenable, or the like. The injection catheter may be steerable, as is known in the art. The injection catheter may be any appropriate length. For example, the injection catheter may be many 3-6 feet long (e.g., for percutaneous procedures entering through the femoral artery for procedures on target tissues located more distally) or shorter (e.g., 4 inches to 3 feet for more proximal entry into the body).

Figure 2A:
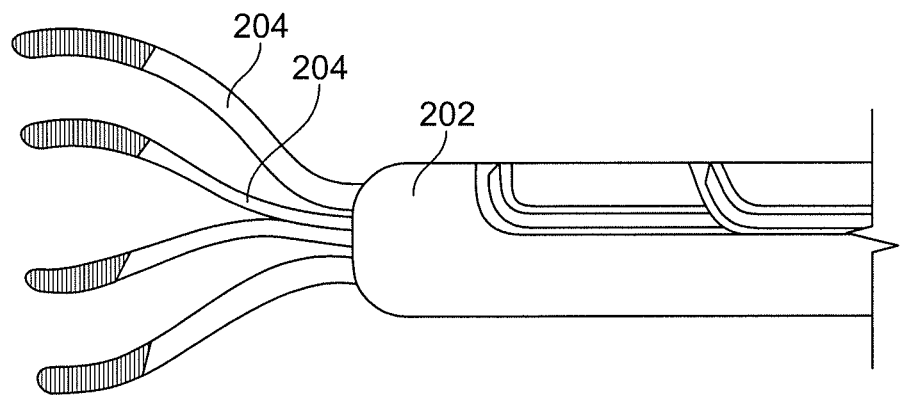
FIGS. 2A-2E show different variations of the injection catheter as described herein.

Injection catheters may also include one or more holdfasts, as described briefly above. A holdfast may be any structure for securing the injection catheter within the vessel lumen. Preferably, the holdfast anchors the injection catheter within the injection lumen without damaging the lumen or causing injury to the subject. In general, the holdfast may releasably attach or secure the catheter within the vessel lumen. FIG. 2A shows some examples of different holdfasts that may be used with injection catheters. For example, in FIG. 2A, the holdfast comprises a plurality of "feet" 204 that project from the body of the injection catheter 202. These feet may be flexible (e.g., they may be made of a spring-like material) so that they can expand to contact the walls of the vessel when released from the body of the catheter. In the example shown in FIG. 2A, the legs of the holdfast are ejected from the distal end of the catheter, and expand outwards to contact the vessel as the legs are extended. The ends of the feet may be configured so that they do not puncture or harm the vessel walls. For example, the feet may be coated in a rubber or silicone. In some variations, the feet may be coated or treated with a material that readily adheres to the walls of the vessel.

Figure 2B:
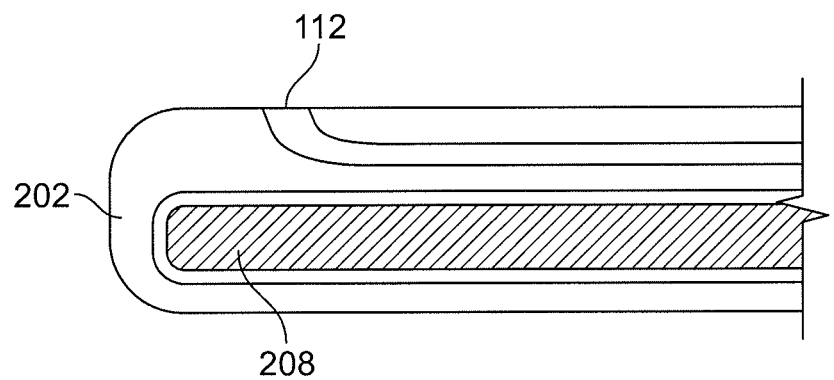

FIG. 2B shows another example of a holdfast, comprising a stiff rod 208 that locks the (otherwise flexible) catheter body into position, at least over the region near the exit port 112 for an injector (not shown). The rigid rod may provide structural support for the injector as it is extended from the injection catheter. In some variations, the injector is coupled to the body of the stiff rod 208, so that the rod provides support for injector (and may steer the injector) as it is extended from the injection catheter.

Figure 2C:
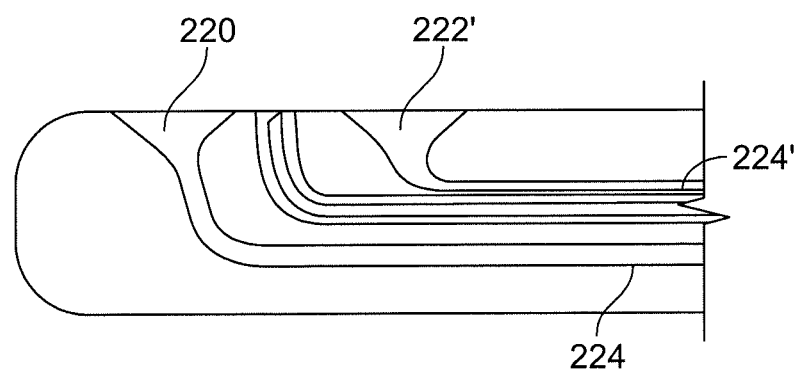

The holdfast shown in FIG. 2C is a vacuum-type holdfast having two vacuum ports 220, 222' that connect (via channels 224, 224') to a vacuum source. A vacuum may be applied through these ports so that when the injection catheter is brought near the vessel wall, the injection catheter will suck onto the wall of the vessel and be held securely. The amount of vacuum may be controlled to prevent damage to the walls of the vessel. Additional variations of the holdfast may be used as well (including the balloon-type holdfasts shown in FIG. 1). As previously mentioned, the injection catheter may include multiple holdfasts which may be positioned in any appropriate way.

The injection catheter also includes one or more injectors, including directional injectors, for injecting fluid (e.g., anesthetic) to a target tissue. Injectors are extendable from the elongate body of the injection catheter. In some variations, the injectors extend from the side of a distal portion of the injection catheter; however they may also extend from the distal end, or from more proximal locations. The injector typically comprises a tissue-penetrating section at the distal end of the injector and a fluid delivery section located proximal to the tissue-penetrating section. The fluid delivery section is configured to deliver fluid in a specific direction, or a selectable direction. In some variations, the fluid delivery section is configured to deliver fluid from the injector in a direction that is different from the direction of tissue penetration.

As previously mentioned, the injector may be manually or automatically extended (and/or retracted). In general, automatically extended injectors may include a trigger that releases the injectors from the body of the catheter. Before it is released, the injector (or injectors) is protected from contacting and possibly damaging the vessel wall as the catheter is positioned. After triggering the automatic release of the injector, at least the distal most tip of the injector is released from the body and extends from the exit port. For example, the injector may be spring loaded so that it is released upon release of a structure (e.g., a sheath or cover) holding it in the catheter. In some variations at least a portion of the injector is formed of (or connected to) a shape memory material (e.g., a nickel titanium alloy) that changes shape to extend the injector.

Figure 2D:
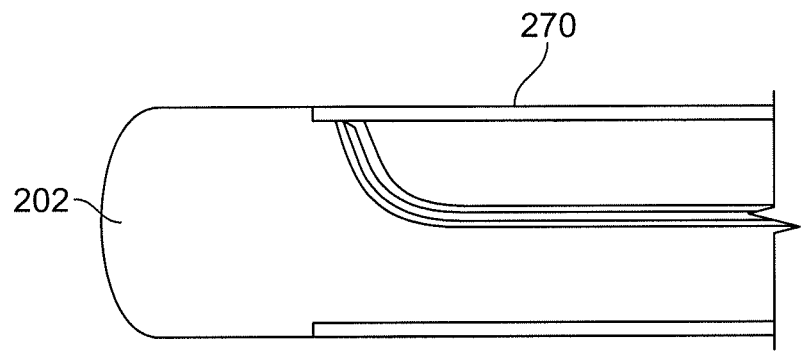
Figure 2E:
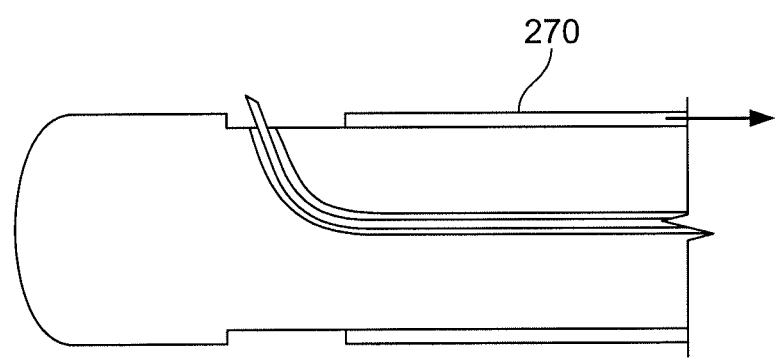

FIGS. 2D-2E shows one variation of an injection catheter having an automatically extending injector. As shown in FIG. 2D, the injector can be kept within the body of the catheter and held secured by a cover 270. The cover has been removed (e.g., by sliding to the right), as shown in FIG. 2E, allowing the injector to be extended from the catheter. In some variations, the injector may also be automatically or manually retracted after it is deployed automatically, (e.g., and the cover 270 may be replaced). In some variations, replacing the cover retracts the injector. Any appropriate trigger may be used, and any appropriate automatic extension may be used (e.g., springs, pneumatic extension, magnetic extension, etc.). The injector shown in FIGS. 2D-2E extends from the body of the injection catheter in a predetermined angle that is not perpendicular to the injection catheter, as shown. In general, the injector may extend from the injection catheter body in any appropriate direction.

In some variations using catheters having one or more automatically extending injectors, the catheter may be positioned, and the injector (or injectors) may be extended. When multiple injectors are used, the same trigger may extend or allow all of the injectors to be extended simultaneously or individually. Once the injector is extended, it may then be positioned against the vessel to allow penetration. This variation (using multiple injectors for simultaneous penetration) may be particularly useful when delivering fluid to the extraluminal space immediately adjacent to the vessel.

The injector may be controlled to determine the direction and extent to which it extends from the catheter. For example, the injection catheter may include a guide, track, or channel (including a keyed channel, as described previously) to control the direction of movement of the injector. In some variations, the injection catheter comprises a deflection plate within the lumen of the catheter to direct the injector (as it is being extended) from the lumen of the catheter through the exit port in a continuous direction. In some variations, this deflection plate can be adjusted to change the angle at which the injector extends from the catheter body.

Figure 3A:
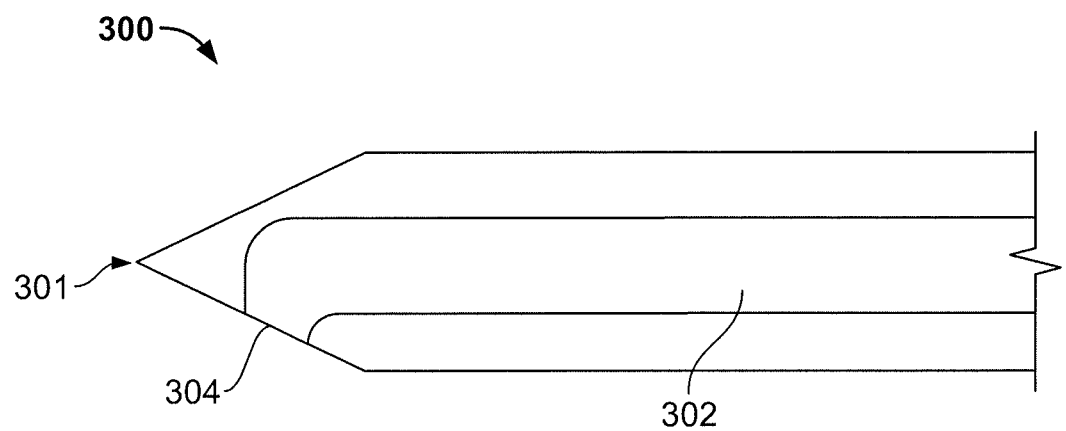
FIGS. 3A-3E show cross-sectional views of different variations of the injectors described herein.
Figure 3B:
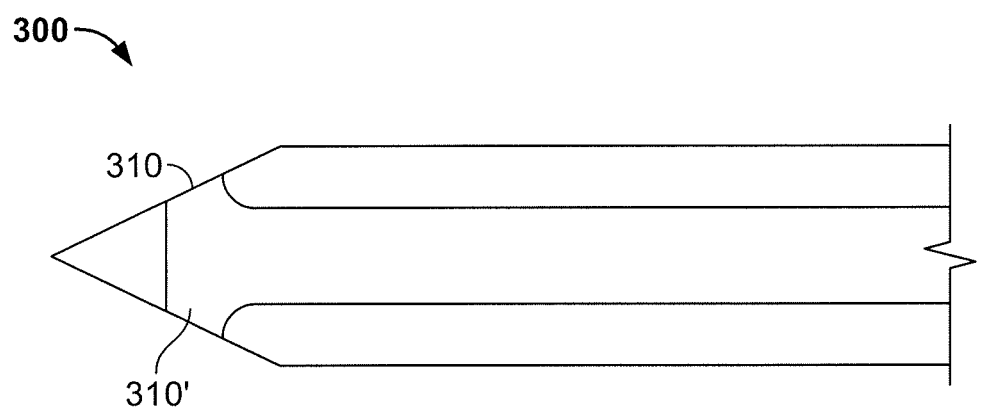
Figure 3C:
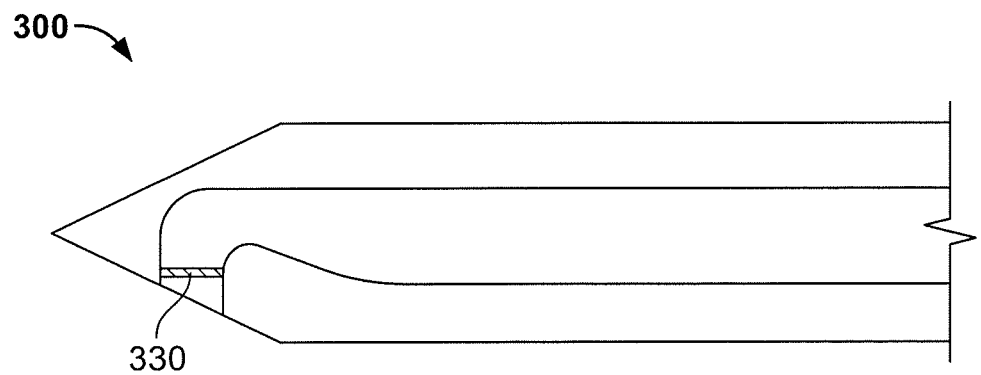
Figure 3D:
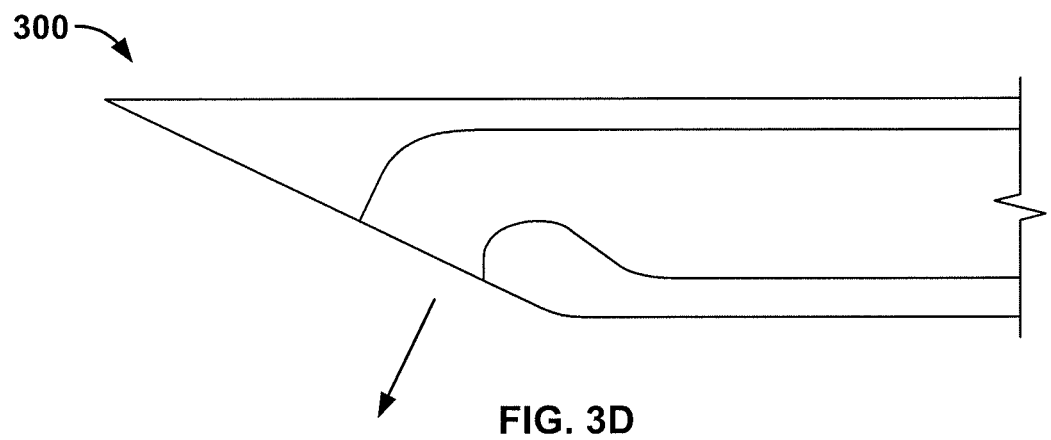

FIGS. 3A-3D show cross-sections of different variations of the tissue-penetrating section and fluid delivery section of directional injectors. For example, FIG. 3A shows the distal end of an injector having a pointed tip 301. The injector contains a passage 302 through which the fluid to be injected can pass. This passage 302 is connected to the opening 304 of the fluid delivery section to allow fluid to be released. As shown in FIG. 3A, the fluid delivery section is located on the angled portion of the tissue-penetrating section, and therefore fluid released from the injector may be released in a direction normal to the angled portion. In this variation, fluid is only released from this one exit of the fluid delivery section. FIG. 3B shows another example in which fluid is released from the fluid delivery section in two places 310,310'. The directional injector maximizes the channeling of fluid along anatomical tissue and fascia planes, allowing the majority of the fluid to efficiently reach the target tissue, even when the target tissue is distant from the injector entry site, without having to reposition the injector.

Figure 3E:
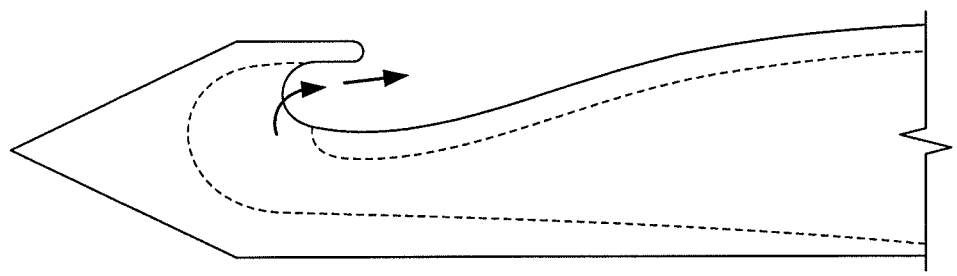

The direction that fluid exits the directional injector may be determined by the configuration of the fluid delivery section. For example, in some variations, the fluid delivery section releases the fluid in a direction that is opposite to the direction of extension of the injector (e.g., in the proximal direction of the injector). FIG. 3E shows one variation of an injector in which fluid exits the injector in the proximal direction (indicated by arrow). Another variation is shown in FIG. 5B.

The flow of fluid from the directional injector may also be regulated, as described above. For example, the directional injector may include buffers, baffles or other structures to prevent fluid leaving the injector from injuring the tissue. For example in FIG. 3C, the fluid delivery section includes a filter 330 through which fluid must pass before it can exit the injector. The internal lumen shape within the injector 302 may also be configured to affect the flow rate and direction of fluid leaving the injector. For example, the lumen may include a widening of the passage to reduce the flow rate as the fluid leaves the injector.

The tissue penetrating region of the injector may be any shape appropriate to penetrate the tissue, including sharp, beveled, pointed, rounded and dull shapes. For example, in FIG. 3D, the injector has a beveled shape. In general, the injector may have an overall needle-shape, allowing it to readily penetrate the tissue. In the examples shown in FIGS. 3A-D, the fluid delivery section is located on the side of the tissue-penetrating section (and the tissue-penetrating section and the fluid delivery section overlap). In some variations, the injector may be a needle having a very small gauge (e.g., 20-30 gauge needle), and the fluid delivery section is located at the distal end of the injector.

Figure 4A:
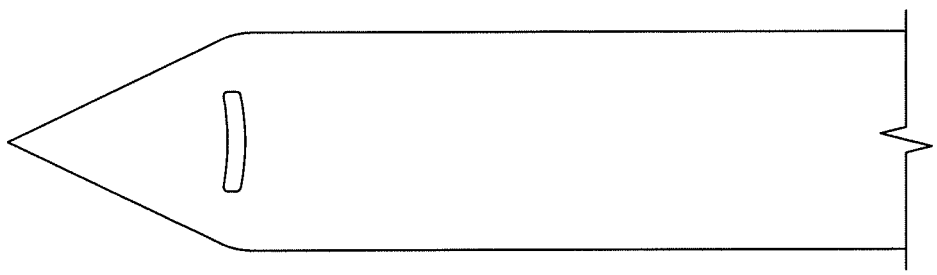
FIGS. 4A-4C show views of different injectors as described herein.
Figure 4B:
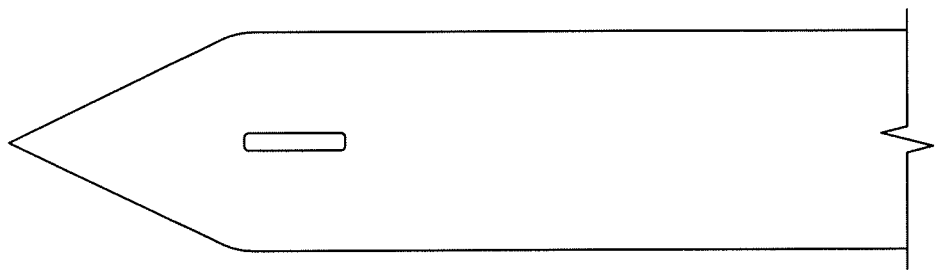
Figure 4C:
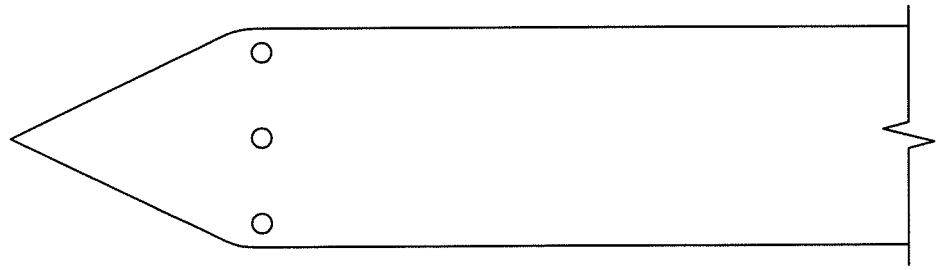

FIGS. 4A-4C show additional views of injectors. In these examples, the fluid delivery section is located more proximally to the tissue-penetrating section. The fluid delivery section comprises exits that are shaped to regulate the flow and direction of fluid therefrom. For example, in FIG. 4A, fluid released from the fluid delivery section would fan out in a plane that is perpendicular to the injector. Similarly, in FIG. 4B, fluid released from the fluid delivery section would be ejected in a plane that is parallel to the injector. Thus, it is possible for the shape and orientation of the fluid delivery section to control the way that fluid is released.

In some variations, different injectors may be used with the same injection catheters. For example, the catheter may have an elongate channel that extends proximally to hold an injector that can be withdrawn and inserted (and extended) through the channel. Thus, injectors may be "swapped out" as needed with other injectors, based on the geometry of the target tissue, or the relationship between the vessel and the target tissue. In some variations this may not be possible, because the injector may be fixed within the injection catheter.

Described below are examples of the methods of using the injection catheters described herein.

EXAMPLE 1

Surgical procedures (particularly percutaneous catheter-based procedures) may cause inappropriate nerve stimulation or even nerve damage. Anesthetizing only the nerve, or a sub-region of the nerve may prevent pain, damage to the nerve, or damage to the patient than can result from improper neural activity. For example, the carotid sinus nerve may be impinged during carotid angioplasty, stent delivery or other procedures performed in the carotid artery. This may cause profound bradycardia or asystole. Clinical evidence suggests that in patients undergoing carotid surgery (endarterectomy), direct application of anesthetic at the bifurcation can render the sinus nerve quiescent.

One variation of the methods described herein is a method of selectively applying anesthetic to a subject's sinus nerve from within the carotid artery to prevent such problems. The method involves inserting an injection catheter into the carotid artery, positioning the injection catheter within the carotid artery near the sinus nerve, anchoring the injection catheter before extending the directional injector of the injection catheter to selectively deliver anesthetic to the sinus nerve, and applying anesthetic from the injection catheter to the sinus nerve.

Figure 5A:
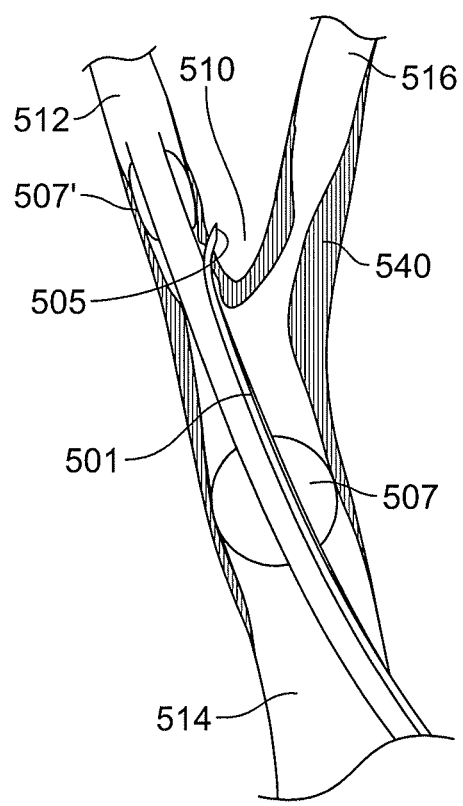
FIGS. 5A-5B show one variation of a method for selectively applying anesthetic to a target tissue.
Figure 5B:
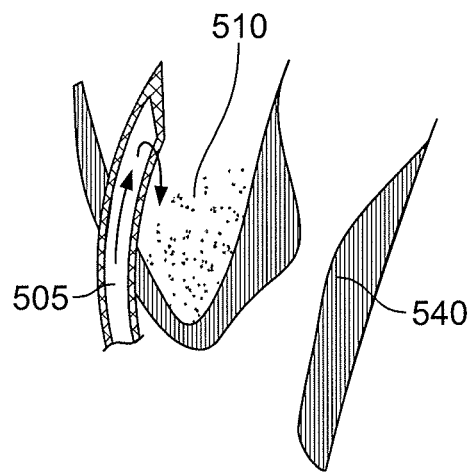

FIGS. 5A and 5B illustrate this method. In FIG. 5A, an injection catheter 501 has been positioned so that the exit port for the injector 505 is adjacent to the carotid sinus 510. The injection catheter 501 straddles the external carotid artery 512 and the common carotid artery 514. The injection catheter 501 has been secured in the artery lumen by the two holdfast balloons 507, 50T attached to the injection catheter 501, and the injector 505 has been advanced into the target tissue, the carotid sinus 510. The distal end of an injector may be coated or filled with a radiodense metal or resin to facilitate visualization of the needle tip. Anesthesia may now be applied within the carotid sinus 510, as shown in the magnified view in FIG. 5B. This procedure may be done in conjunction with the TOPS procedure described briefly above, in which the flow of blood through the common carotid artery and the external carotid artery are arrested so that internal carotid artery backpressure sweeps dislodged debris into a lower pressure reservoir, allowing repair of lesions or other procedures. For example, in FIGS. 5A and 5B, the internal carotid artery is shown having a buildup of stiff plaque 540. Removal of this plaque (e.g., by angioplasty, scraping, etc.) may otherwise improperly stimulate or impinge on the sinus nerve. The method described herein may be used to apply anesthetic to reduce unwanted effects.

Providing anesthetic to nerves such as the sinus nerve is particularly useful before performing intravascular procedures near the nerve. For example, during angioplasty procedures, it may be beneficial to provide anesthetic to nearby nerves (such as the sinus nerve) before beginning the angioplasty procedure, while avoiding involvement with the recurrent laryngeal nerve, phrenic nerve, superior laryngeal nerve, hypoglossal nerve, facial nerve, or vagus nerve. Indiscrete application of anesthetic to these nerves can occur immediately or through diffusion from larger volumes of anesthetic delivered without directional application. This may result in detrimental changes to speech, respiration, swallowing and facial expression, leading to poor subject experience, difficulty communicating, respiratory distress, and aspiration pneumonia.

EXAMPLE 2

The devices and methods described herein may also be used to improve surgical procedures on the vessels themselves. For example, fluid may be used to fill the space in the fascia around the vessel so that it swells or becomes tumescent. This both narrows the vessel (making it easier to ablate or operate on) and may separate the walls of the vessel that are subject to the heat or pressure of the surgery from adjacent structures that may otherwise be injured. Tumescence is generally temporary, as the fluid is absorbed by the tissue over time. This procedure may be referred to as tumescent anesthesia.

In typical tumescent anesthesia, a small needle (e.g., 27 to 30 gauge) is generally used from outside of the body to first numb the skin in multiple locations, and then a larger needle (e.g., 19 to 25 gauge) is used to load the larger volume of tumescent fluid at an acceptable rate again at multiple locations. However, this method is both inaccurate, time consuming, and potentially dangerous, as it risks injuring other regions of tissue than the target region. In particular, when the procedure to be followed involves operating on the walls of a vessel (e.g., by ablating with electrical energy), it would be much better to apply fluid beneath the fascia surrounding the vessel, so as to insulate nearly tissue structures. For example, tumescent anesthesia may be helpful when applying heat, laser, or electrical energy to ablate regions of a blood vessel wall.

In general, blood vessels follow the same histological makeup: the inner lining is the endothelium, followed by subendothelial connective tissue, and then a muscular layer of vascular smooth muscle. Finally, there is a further layer of connective tissue (adventitia), which contains nerves that supply the muscular layer, as well as nutrient capillaries in the larger blood vessel. The blood vessel may be within a fascial layer. Thus, the methods described herein may be used to apply fluid (including but not limited to fluid containing anesthesia) to create tumescence between these layers (e.g., between the adventitia and the fascial layer).

In this procedure, fluid is injected into the tissue from within the blood vessel, rather than external to the subject, avoiding the separate punctures of the skin. The injection catheter may comprise any of the catheters described above, and may have an injector with a delivery tube for the anesthetic solution that is in the 21 to 30 gauge range for remote instillation of fluid into the extraluminal space. Furthermore, the region of the vessel made tumescent by the method described herein may be specific to the region that will be treated. In some variations, the injection catheter used to inject the solution causing tumescence may include one or more ablation electrodes for treating the vessel.

Figure 6A:
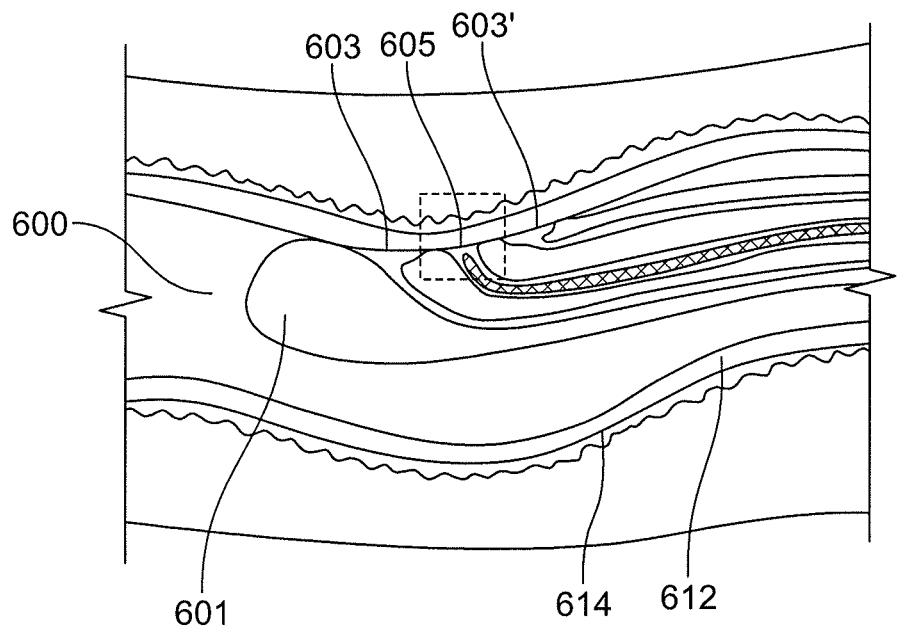
FIGS. 6A, 6B and 6C illustrate one variation of a method for creating tumescence from an injection site within a vessel, as described herein.
Figure 6B:
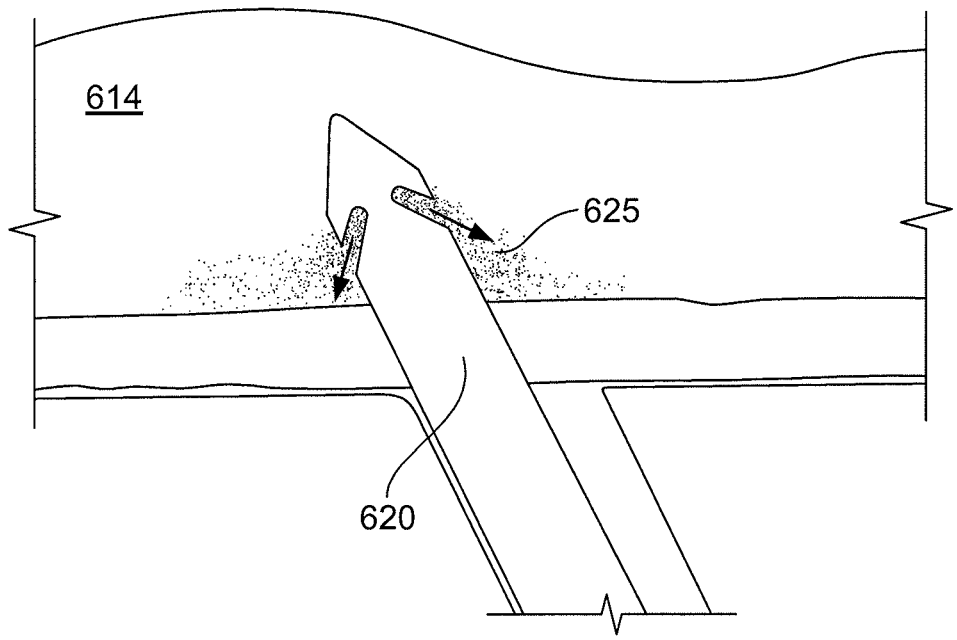
Figure 6C:
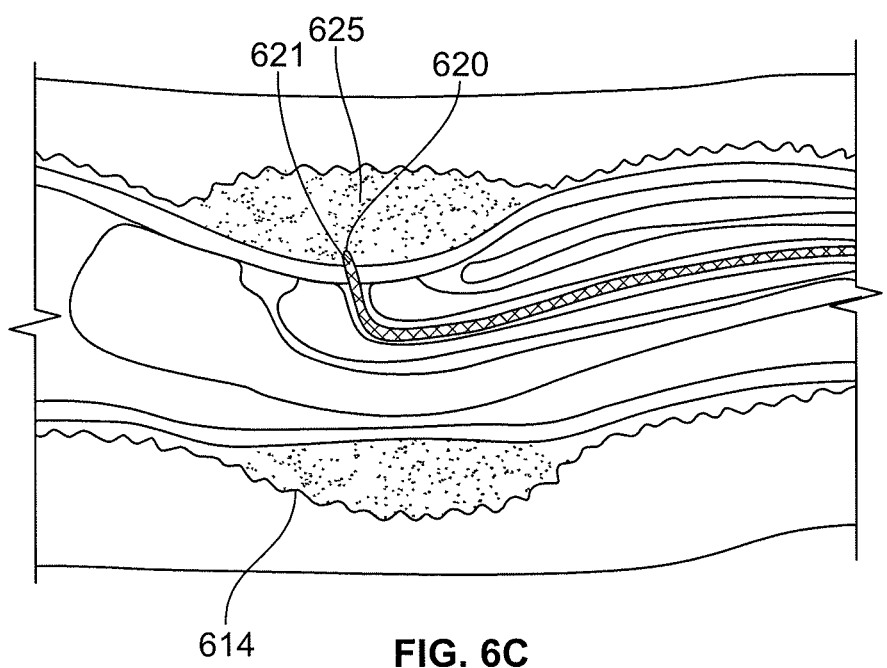

Any appropriate amount of fluid used to create the tumescence may be added, and this may be monitored by ultrasound. Generally, even though fluid enters the extraluminal space from a single insertion (e.g., a single injector), the fluid may spread to surround the vessel, following the planes of the fascia in the space between the adventitia and the fascial layer (e.g., the subfascial layer). FIGS. 6A-C illustrates this method.

In FIG. 6A an injection catheter 601 has been positioned within a vein 600, as described, and the holdfast (here consisting of two suction-type holdfasts 603, 603' surrounding the injector exit port 605) has secured the injection catheter against the wall of the vein 600. The endothelium 612 and subfascial layer 614 are also indicated. FIG. 6B shows a magnified view of the injector from FIG. 6A after it has been extended into the subfascial layer 614 (also shown in FIG. 6C), and has begun applying fluid 625 (schematically illustrated by the speckled pattern). The fluid is released by the injector in a substantially proximal direction with respect to the injector (as indicated by the arrows). Thus, the fluid 625 is released into the layer 614, and the force of release of the fluid does not damage the tissue or impinge on neighboring layers. In addition, the layer will serve as a channel or guide for the fluid.

FIG. 6C shows the injector 620 after it has injected a substantial amount of fluid 625 into the subfascial layer 614, creating tumescence which has both reduced the diameter of the vessel 600, and has increased the distance between the outer wall of the vessel 612 and any nearby structures. Once adequate tumescence has been established (as viewed by ultrasound, for example), the injector can be withdrawn and the catheter advanced to a nearby region if further tumescence of this vessel is desired. The vessel can then be treated, e.g., by ablation or application of energy.

In this example, the structure is anesthetized by the addition of a solution containing anesthesia to create tumescence and it is localized with ultrasound guidance. As described above, the solution need not contain anesthesia. Furthermore, although this example shows a vacuum-type holdfast, any appropriate holdfast (or injector) may be used as part of the injection catheter.

Without the methods described herein, the use of tumescent anesthesia is both difficult and potentially dangerous. For example, in thin patients, the tumescent fluid must be applied just under the skin where it is hard to see the needle. In deep structures, the needle may not be easily visualized or multiple adjustments may be needed to the ultrasound probe orientation to align it with the needle and the structure to be treated. For example, the treatment of the short saphenous vein in the posterior calf currently requires the patient to be supine or in an awkward bent position to allow sufficient space to place the ultrasound probe and to allow the operator to see the alignment of the needle to the ultrasound probe. Treatment in the supine position requires repositioning, repreparing and redraping of the patient to subsequently treat veins on the anterior surface of the body.

The use of the methods and apparatuses described herein can also be applied to procedures such as radiofrequency or laser ablation of venous structures for varicose veins or chronic venous stasis. Both techniques have an incidence of parasthesias from injured nerves that run adjacent to the vein. Heat energy that is not effectively buffered by tumescent fluid may result in damage to subcutaneous and skin tissues. In particular, the increased incidence of post procedure bruising and pain from treatment with the hotter laser catheter may be avoided using endolumenal tumescent injection that more accurately deploys a greater volume of tumescent fluid adjacent to the vein and avoids skipping areas resulting in poor tumescence.

Furthermore, the space from skin to the vessel created by the tumescent fluid layer decreases with time as fluid diffuses into the surrounding tissues. The direct application of fluid to the perivascular space alone and the ability to easily instill fluid at the time of active ablation allow maximal separation of the heat source from nerve, skin and subcutaneous tissue. The fluid can also be cooled down (e.g., to near freezing) to further reduce damage to surrounding tissues. The method of endolumenal delivery of tumescent anesthesia can allow direct placement of fluid adjacent to the active heating element used for ablation, and this fluid can absorb some of the heat energy before it has a chance to harm adjacent structures. This could be particularly useful for treating the short saphenous vein where the nerve courses more closely with the vessel. Currently, the most prudent approach used is to treat a short segment of the proximal vein where the nerve is generally more separated from the vein. This method is less desirable than the method outlined herein, because treatment of a short segment increases the risk of failed closure of the vein or reflux of blood from branches below the treated vein. The techniques described above may enable safe treatment of a longer length of vein, thereby improving results.

While the invention has been described in terms of particular variations and illustrative figures, those of skill in the art will recognize that the invention is not limited to the variations or figures described. In addition, where methods and steps described above indicate certain events occurring in certain order, those of skill in the art will recognize that the ordering of certain steps may be modified and that such modifications are in accordance with the variations of the invention. Additionally, certain steps may be performed concurrently in a parallel when possible, as well as performed sequentially as described above. Therefore, to the extent there are variations of the invention which are within the spirit of the disclosure or equivalent to the inventions found in the claims, it is the intent that this patent will cover those variations as well. Finally, all publications and patent applications cited in this specification are herein incorporated by reference in their entirety as if each individual publication or patent application were specifically and individually put forth herein.

What is claimed:

1. A method of applying anesthetic to a target structure from within a body vessel without substantially applying anesthetic to non-target structures, the method comprising:
    inserting an injection catheter into a body vessel, wherein the injection catheter comprises a directional injector configured to apply anesthetic selectively to the target structure, wherein the target structure comprises a region surrounding the sinus nerve;
    positioning the injection catheter within the body vessel near the target structure;
    anchoring the injection catheter by deploying a stiff member to which the injection catheter couples;
    extending the directional injector to deliver anesthetic to the target structure; and
    applying anesthetic from the injection catheter to the target structure.

2. The method of claim 1, further comprising the step of visualizing the injection catheter.

3. The method of claim 2, further comprising visualizing the injection catheter by fluoroscopic visualization.

4. The method of claim 1, further comprising the step of visualizing the application of anesthetic to the target structure.

5. The method of claim 4, wherein the step of visualizing the application of anesthetic to the target structure comprises releasing radiopaque substance with the anesthetic.

6. The method of claim 1, wherein the step of extending the directional injector comprises monitoring the orientation of the directional injector so that the directional injector is positioned near the target structure.

7. The method of claim 1, wherein the step of anchoring the injection catheter comprises inflating a balloon connected to the injection catheter to secure the injection catheter within the body vessel.

8. The method of claim 1, wherein the target structure comprises the sinus nerve.

* * * * *